United States Patent [19]

Mericle

[11] 4,214,586
[45] Jul. 29, 1980

[54] ANASTOMOTIC COUPLING DEVICE

[75] Inventor: Robert W. Mericle, Bridgewater, N.J.

[73] Assignee: Ethicon, Inc. Somerville, N.J.

[21] Appl. No.: 965,448

[22] Filed: Nov. 30, 1978

[51] Int. Cl.² .................. A61B 17/04; F16L 17/00; F16L 19/00; F16L 21/02
[52] U.S. Cl. .................. 128/334 R; 285/370
[58] Field of Search ............. 128/334 R, 334 C, 247; 285/259, 371, 418, 370, 397, 319, 55, DIG. 22; 403/305

[56] References Cited

U.S. PATENT DOCUMENTS

| | | | |
|---|---|---|---|
| 517,192 | 3/1894 | Prior | 285/319 |
| 824,753 | 7/1906 | Stephens | 285/259 |
| 2,388,992 | 11/1945 | Pape et al. | 285/259 |
| 2,453,056 | 11/1948 | Zack | 128/334 |
| 3,155,095 | 11/1964 | Brown | 128/334 C |
| 3,221,746 | 12/1965 | Noble | 128/334 |
| 3,226,137 | 12/1965 | Trnka | 285/371 |
| 3,254,650 | 6/1966 | Collito | 128/334 |
| 3,496,939 | 2/1970 | Odiaga et al. | 128/334 |
| 3,563,573 | 6/1971 | Crompton et al. | 285/55 |
| 3,588,149 | 6/1971 | Demler, Sr. et al. | 285/319 |
| 3,640,552 | 2/1972 | Demler, Sr. et al. | 128/247 UX |
| 3,683,926 | 8/1972 | Suzuki | 128/334 R |
| 3,774,615 | 11/1973 | Lim et al. | 128/334 C |
| 3,797,499 | 3/1974 | Schneider | 128/334 R |
| 3,974,835 | 8/1976 | Hardy, Jr. | 128/334 C |
| 4,137,921 | 2/1979 | Okuzumi et al. | 128/335.5 |

OTHER PUBLICATIONS

Surgery, The Use of Rigid and Flexible Plastic Prostheses for Arterial Replacement, vol. 37, No. 2 Feb. 1955, pp. 165-174.

*Primary Examiner*—Robert W. Michell
*Assistant Examiner*—C. W. Shedd
*Attorney, Agent, or Firm*—Wayne Ebehardt

[57] ABSTRACT

A three-piece anastomotic coupling device for end-to-end anastomosis of tubular members consisting of two open bore cylindrical adaptors and an open bore cylindrical connector. Each end of a tubular member is passed through the axial bore of an adaptor and everted over the end thereof. The adaptors are then inserted into opposite ends of the connector until the everted ends of the vessel abut under light compression. Integral locking means are provided to secure the adaptors and tubular members of the connector piece.

20 Claims, 7 Drawing Figures

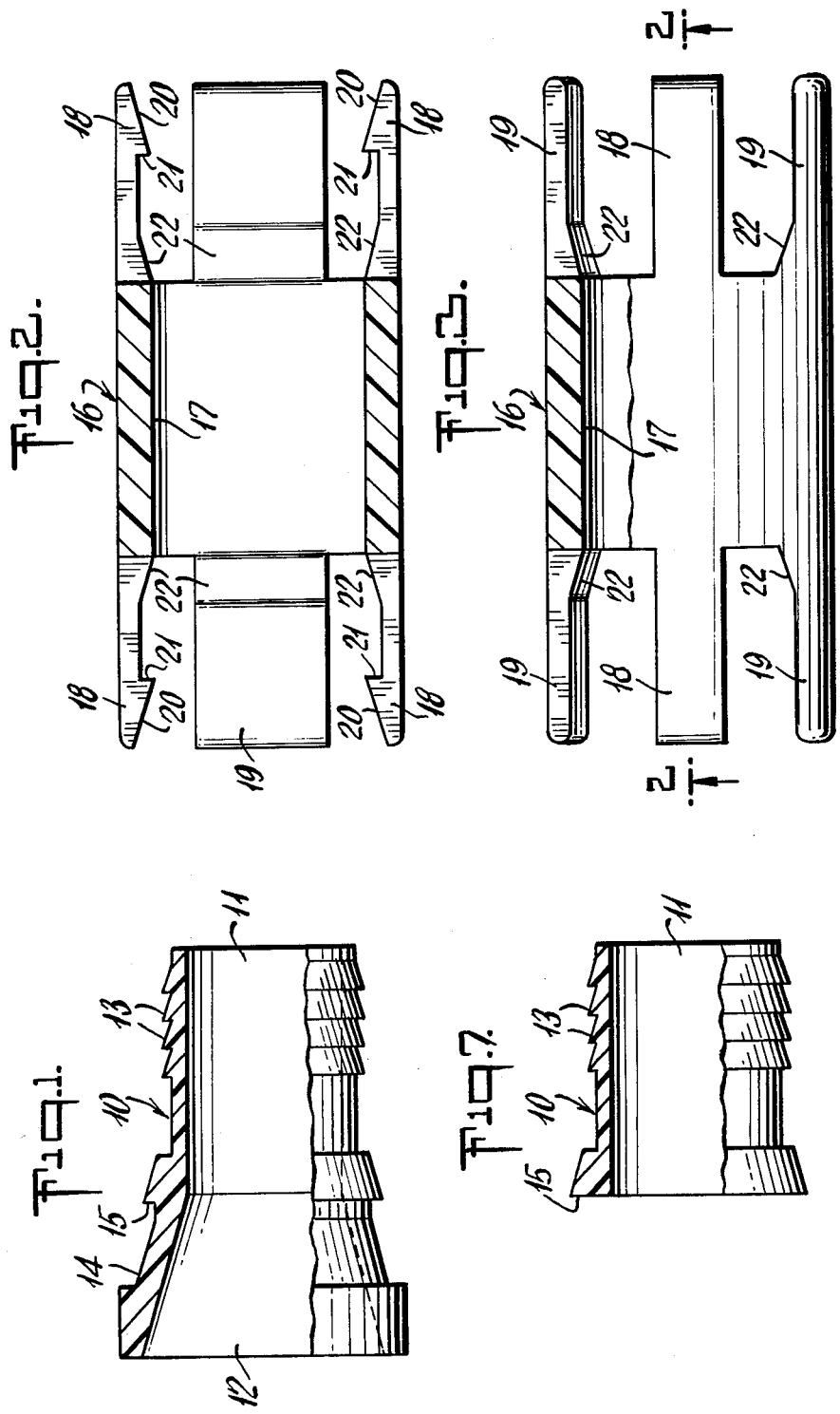

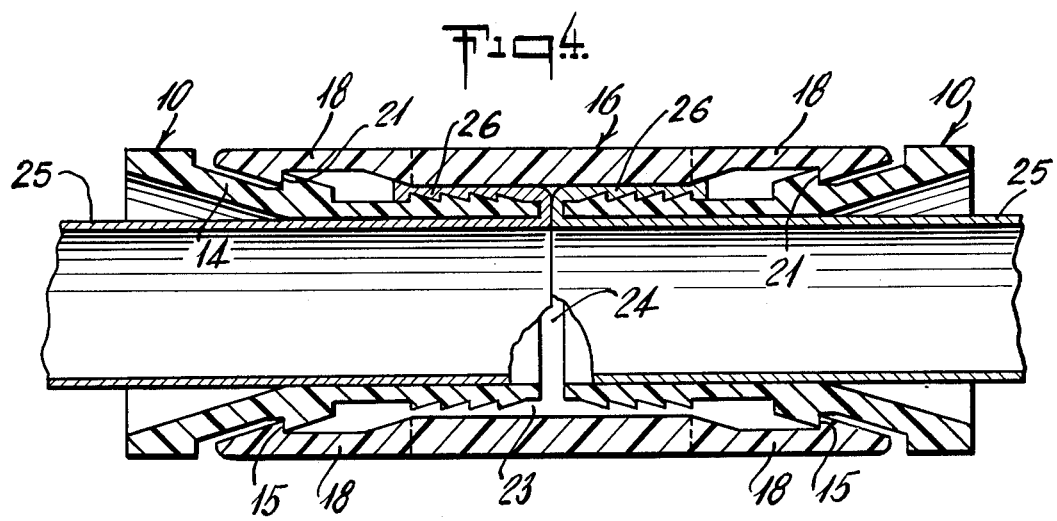
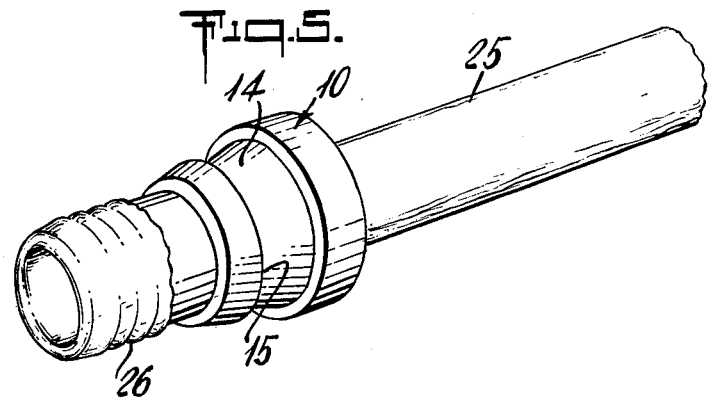
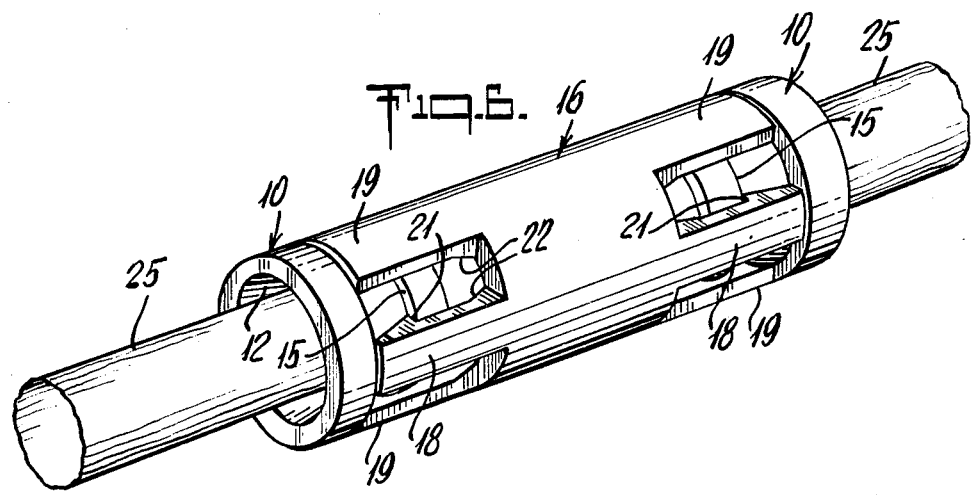

ANASTOMOTIC COUPLING DEVICE

BACKGROUND OF THE INVENTION

The present invention relates to devices for end-to-end anastomosis of tubular organs, and more particularly, to anastomotic coupling devices for reconnecting the ends of severed blood vessels in a manner to promote the healing thereof.

End-to-end anastomosis of severed vessels may be accomplished either by suturing, stapling or mechanical coupling. Suturing is generally difficult to perform, especially when very small vessels are involved, and requires great skill and experience on the part of the surgeon. Suturing is also susceptible to complications resulting from damage to the vascular wall, leakage, and potential harboring of infection around the suture material.

Stapling and mechanical coupling of blood vessels has been suggested to avoid the disadvantages of suturing, and to provide a faster, more reliable and relatively simple method of anastomosis. Various designs for mechanical coupling devices have been proposed, as for example, in U.S. Pat. Nos. 2,453,056; 3,221,746; 3,254,650; 3,774,615; and 3,974,835.

The ideal anastomotic coupling device should provide perfect adaptation of the vascular members without damage to the vascular wall, and be completely external of the vascular lumen. In addition, the device must provide for quick, sure placement with a minimal possibility for error on the part of the surgeon.

It is accordingly an object of the present invention to provide an anastomotic coupling device providing the aforesaid characteristics. It is a further object of this invention to provide an anastomotic coupling device particularly adapted for joining small blood vessels. A yet further object of this invention is to provide a device for joining the ends of interrupted tubular organs of various sizes and functions, including, for example, veins, arteries, lymphatic ducts, oviducts, ureters, intestines, and the like. These and other objects of the present invention will be evident from the ensuing description and claims.

SUMMARY

The anastomotic coupling device of the present invention consists of three pieces: two tubular adaptors and one interlocking connector piece. Preferred adaptors consist of an open cylindrical section terminating at one end in an expanding truncated conical section. The exterior surface of the conical section is provided with means for interlocking with said connector piece as hereinafter described.

The connector piece preferably consists of an open cylinder terminating at each end in extensions having means thereon for interlocking with said adaptors when said adaptors are inserted into said connector.

In application, one end of the tubular member to be joined is passed through the conical section and cylindrical section of one adaptor and everted over the end of the cylindrical section. The exterior surface of the cylindrical section is preferably provided with means for gripping the everted end of the tubular member.

The second adaptor is secured to the end of the other tubular member in a like manner.

One adaptor with the tubular member everted theron is inserted into one end of the connector and the locking means on the conical section of said adaptor interlocked with the locking means on the extensions of said connector. The second adaptor with the tubular member everted thereon is inserted into the other end of the connector and interlocked therewith in a like manner to complete the connection of the tubular member.

The inside diameter of the cylindrical section of the connector is greater than the outside diameter of the cylindrical section of the adaptor by an amount sufficient to accommodate the wall thickness of the everted tubular member. Preferably, the diameters are sized so that a small compressive force is exerted on the wall of the tubular member in the assembled connector.

The length of the cylindrical section of each adaptor is sized so that when assembled in the connector, the ends of the adaptors are spaced apart by a distance slightly less than twice the wall thickness of the tubular member. In this manner, the intimal surfaces of the everted ends of the tubular member are brought into contact under light compression which is effective to prevent leakage and is desirable to promote healing of the joined tissue.

The coupling device is completely external to the lumen of the tubular organ, and intraluminal juncture between the two ends is smooth and uniform. The flow of blood or other fluid through the tubular organ is thereby maintained without disruption or stagnation which could result in thrombosis or promote infection.

DESCRIPTION OF DRAWINGS

FIG. 1 is a plan view in partial cross section of an adaptor for the coupling device.

FIG. 2 is a view in cross section of a connector for the coupling device.

FIG. 3 is a plan view in partial cross section of the connector of FIG. 2, rotated 90 degrees.

FIG. 4 is a view in cross section of an assembled coupling device with the tubular member shown in partial section for clarity.

FIG. 5 is a view in perspective of one adaptor attached to the end of a tubular vessel.

FIG. 6 is a view in perspective of a tubular member connected by means of the coupling device of FIG. 4.

FIG. 7 is a plan view in partial cross section of a variation of the adaptor of FIG. 1.

DESCRIPTION OF PREFERRED EMBODIMENTS

Referring now to FIG. 1, there is illustrated in partial cross section adaptor 10 consisting of cylindrical section 11 and expanding truncated conical section 12. A plurality of annular ridges 13 circumscribe the outer circumference of section 11 over an area extending from the open end thereof. A single annular recess 14 circumscribes conical section 12 and forms locking ridge 15, the surface of which is in a plane substantially vertical to the axis of the adaptor.

FIG. 2 illustrates in cross section a connector indicated generally as 16 for use with the adaptor of FIG. 1. Connector 16 consists of a central cylindrical section 17 having locking appendages 18 and guiding appendages 19 extending from either end thereof. As illustrated, locking appendages 18 are located on the vertical axis of the connector, and each appendage has distal locking means consisting of a beveled surface 20 forming ridge 21 on the inner surface thereof, the surface of ridge 21 being in a plane substantially vertical to the axis of the connector.

Also, as illustrated in FIG. 2, guiding appendages 19 are located on the horizontal axis of the connector. Appendages 19 serve as guides during the assembly of the coupling and are not provided with locking means as best seen in the cross-sectional view of FIG. 3.

Referring further to FIG. 2 and FIG. 3, appendages 18 and 19 are beveled at 22 in order to increase the effective inside diameter of the partial cylinder defined by the appendages and thereby facilitate and guide the insertion of the adaptors into the connector.

Referring now to FIG. 4, there is illustrated a fully assembled coupling device according to FIGS. 1 and 2 with the tubular member shown in partial section for clarity. Adaptors 10 are inserted into connector 16 until locking appendages 18 engage annular recess 14 in the adaptor, at which time ridge 21 of appendage 18 abuts ridge 15 of the adaptor locking the adaptor securely in place. Bevel 20 on appendage 18 guides the distal end of the appendage over the conical section of the adaptor and into annular recess 14.

Guide appendages 19 (not shown in FIG. 4), in cooperation with locking apendages 18, assure positive positioning of the adaptor in the connector, and the dual locking appendages on opposing sides of the adaptor secure the adaptor firmly in position.

In the assembled coupling there is provided a design space 23 between the outside diameter of the cylindrical section of the adaptor and the inside diameter of the cylindrical section of the connector. Space 23 serves to accommodate the wall of the tubular member which is everted over the end of the adaptor before assembly of the coupling. Preferably, the width of space 23 is slightly less than the wall thickness in order to apply a light compressive force on the everted wall of the tubular member.

The assembled coupling also provides design space 24 between opposing ends of the adaptors in order to accommodate the double wall thickness of the everted ends of the tubular members. The width of space 24 is preferably slightly less than twice the wall thickness in order to apply a compressive force on the everted walls of the tubular members sufficient to prevent leakage through the junction. A light compressive force also assures a smooth, continuous, intraluminal junction between the everted ends of the tubular members and minimize any disruption of laminar flow within the lumen of the vessel.

The assembly of an adaptor to a severed end of a tubular member is illustrated in FIG. 5 where vessel 25 is passed through the cylindrical bore of adaptor 10 and end 26 of vessel 25 is everted over the cylindrical section of the adaptor. Preferably, the everted portion of the vessel extends at least half way over the cylindrical section of the adaptor and sufficiently over gripping means 13 on the external surface of the adaptor to secure the adaptor on the vessel.

A fully assembled anastomotic coupling device joining the severed ends of a tubular member is illustrated in FIG. 6.

The adaptor of FIG. 1 may be simplified by omitting all or a major portion of the conical section as illustrated in FIG. 7. This design simplifies fabrication of the piece and reduces the mass of foreign material to be implanted in the body which may be desirable under certain circumstances. The simplified design has a disadvantage, however, in being more difficult to handle and to assemble in the coupling device.

The anastomotic coupling device of the present invention may be constructed in a variety of sizes, and is especially useful in connecting very small vessels, i.e., 1 to 5 mm OD, which are particularly difficult to suture. The adaptors of the coupling device should have an inside diameter approximately equal to the outside diameter of the vessel for best results.

The coupling device may also be fabricated in larger sizes corresponding to the outside diameters of large veins, arteries, and intestines, and may furthermore be used to join natural tubular members to synthetic devices such as vascular prostheses of Dacron or Teflon.

The coupling devices may be fabricated by any convenient means such as machining or molding, and of a variety of materials which are known to be biocompatible in surgical applications. Nylon, polypropylene, and polysulfone are illustrative of polymeric materials which are readily shaped into the miniature pieces of the coupling device. The device may also be fabricated of stainless steel, or of biologically absorbable materials such as polyactide, polyglycolide, and copolymers of lactide and glycolide which are known to hydrolyze in tissue with eventual complete absorption by the body.

The preceding description has been largely directed to preferred embodiments of the present invention, and many variations thereof will be apparent to those skilled in the art. For example, one or more locking appendages 18 may be substituted for each guiding appendage 19 illustrated in FIG. 4, and various means for interlocking the end pieces and the connector piece may be employed without departing from the spirit or scope of the present invention. In addition, vessel gripping means 13 illustrated in FIG. 1 may be omitted, or other gripping means such as a knurled surface or miniature spikes may be substituted for the annular rings of the illustration.

The essential element of the present invention is a three-piece coupling device for end-to-end anastomosis of tubular members comprising two adaptors, each sized to receive the severed end of a tubular member with the end of the member everted over the adaptor, and a cylindrical connector sized to receive and secure each adaptor individually with the everted ends of the tubular member in abutment within said connector.

What is claimed is:

1. A three-piece anastomotic coupling device for end-to-end anastomosis of tubular members comprising two adaptors and a connector, each of said adaptors comprising a cylinder having an axial bore therethrough sized to receive one tubular member with the end of said member everted over the end of said adaptor, said connector comprising a cylinder having an axial bore therethrough sized to receive each of said adaptors and the tubular member everted thereover in opposing ends of said cylinder with the everted ends of the tubular members in abutting contact within said cylinder, and means for interlocking said adaptors and said connector to maintain the everted ends of the tubular members in contact.

2. A device of claim 1 wherein said adaptors include means for gripping the everted end of the tubular member received therein.

3. A device of claim 2 wherein said gripping means comprise a plurality of raised annular rings around the outer circumference of said adaptor.

4. A device of claim 1 wherein the inside diameter of the axial bore of the connector exceeds the outside diameter of the cylinder of the adapter by an amount sufficient to accommodate the wall thickness of the everted tubular member.

5. A device of claim 1 wherein the ends of the adaptors in the assembled device are spaced apart by a distance sufficient to accommodate the combined wall thickness of the everted tubular members.

6. A device of claim 1 wherein said means for interlocking said adaptors and said connector comprise appendages extending from each end of said cylindrical connector piece, said appendages having an inward facing lip on the distal end thereof, and an annular ridge having an outward facing surface circumscribing each of said adaptors, said ridge being engaged by said lip to retain said adaptor in said connector.

7. A device of claim 1 fabricated of a biocompatible polymeric material.

8. A device of claim 7 wherein said material is absorbable in a biological system.

9. A device of claim 8 wherein said material is selected from the group consisting of homopolymers and copolymers of lactide and glycolide.

10. A device of claim 7 wherein said material is selected from the group consisting of nylon, polypropylene and polysulfone.

11. A device of claim 1 wherein the diameter of the axial bore in the cylinder of the adaptor is 1 to 5 mm.

12. A three-piece anastomotic coupling device for joining the severed ends of a tubular member comprising two adaptors and an interlocking connector, each of said adaptors comprising a cylinder having an axial bore therethrough terminating at one end in a plane normal to the axis of the bore and at the other end in an expanding truncated conical member, means on the exterior surface of said conical member for interlocking with corresponding means on said connector piece, and means on the exterior surface of the plane end of said cylinder for gripping a tubular member everted thereover, said connector comprising a cylinder having an axial bore therethrough, and terminating at each end in appendages extending therefrom and having means on the interior surfaces at the distal ends thereof for interlocking with corresponding means on said adaptors, the inside diameter of the cylinder of said connector being larger than the maximum outside diameter of the cylinder of the adaptor, and the length of each adaptor being such that the ends of the adaptors are spaced apart when interlocked with said connector in the assembled coupling device, whereby each end of the tubular member to be joined may be passed through the conical member and cylinder of each adaptor and everted over the end thereof, and said ends of said adaptors and everted tubular members thereon may be inserted into opposite ends of said connector and interlocked therewith with the intimal surfaces of the everted tubular members abutting one another.

13. A device of claim 12 wherein the gripping means for the everted tubular members comprise a plurality of raised, annular rings around the outer circumference of the cylinder of the adaptor.

14. A device of claim 12 wherein the inside diameter of the connector is larger than the outside diameter of the adaptor by an amount sufficient fo accommodate the wall thickness of the everted tubular member.

15. A device of claim 12 where the adaptors in the assembled coupling device are spaced apart by a distance sufficient to accommodate the combined wall thickness of the everted tubular members.

16. A device of claim 12 fabricated of a biocompatible polymeric material.

17. A device of claim 16 wherein said material is absorbable in a biological system.

18. A device of claim 17 wherein said material is selected from the group consisting of homopolymers and copolymers of lactide and glycolide.

19. A device of claim 16 wherein said material is selected from the group consisting of nylon, polypropylene and polysulfone.

20. A device of claim 12 wherein the diameter of the axial bore in the cylinder of the adaptor is 1 to 5 mm.

* * * * *